United States Patent
Sabesan et al.

(10) Patent No.: US 8,524,474 B2
(45) Date of Patent: Sep. 3, 2013

(54) PROCESS FOR PRODUCING A CONCENTRATED SUGAR SOLUTION BY ENZYMATIC SACCHARIFICATION OF POLYSACCHARIDE ENRICHED BIOMASS

(75) Inventors: Subramaniam Sabesan, Wilmington, DE (US); Christina Jacy Spado, Philadelphia, PA (US)

(73) Assignee: E I du Pont de Nemours and Company, Wilmington, DE (US)

( * ) Notice: Subject to any disclaimer, the term of this patent is extended or adjusted under 35 U.S.C. 154(b) by 338 days.

(21) Appl. No.: 12/621,579

(22) Filed: Nov. 19, 2009

(65) Prior Publication Data

US 2010/0124770 A1 May 20, 2010

Related U.S. Application Data

(60) Provisional application No. 61/116,382, filed on Nov. 20, 2008, provisional application No. 61/116,386, filed on Nov. 20, 2008.

(51) Int. Cl.
| | |
|---|---|
| *C12P 7/10* | (2006.01) |
| *C12P 19/00* | (2006.01) |
| *D21C 1/00* | (2006.01) |
| *D21C 3/02* | (2006.01) |
| *D21C 3/22* | (2006.01) |

(52) U.S. Cl.
USPC ........ 435/165; 435/72; 435/277; 162/70; 162/90

(58) Field of Classification Search
None
See application file for complete search history.

(56) References Cited

U.S. PATENT DOCUMENTS

| | | | | |
|---|---|---|---|---|
| 3,844,890 | A | * | 10/1974 | Horikoshi et al. ........... 435/209 |
| 4,072,538 | A | | 2/1978 | Fahn et al. |
| 4,904,599 | A | * | 2/1990 | Ozaki et al. ............ 435/252.33 |
| 4,962,030 | A | * | 10/1990 | Kawai et al. ............... 435/209 |
| 5,407,827 | A | * | 4/1995 | Casimir-Schenkel et al. ............... 435/278 |
| 5,503,996 | A | | 4/1996 | Torget et al. |
| 5,916,780 | A | | 6/1999 | Foody et al. |
| 6,376,445 | B1 | * | 4/2002 | Bettiol et al. ................ 510/320 |

(Continued)

FOREIGN PATENT DOCUMENTS

| | | |
|---|---|---|
| WO | 0237981 A2 | 5/2002 |
| WO | 2008065433 A1 | 6/2008 |
| WO | 2008095098 A2 | 8/2008 |
| WO | 2008134037 A1 | 11/2008 |

OTHER PUBLICATIONS

Silverstein, Rebecca A. et al., A comparison of chemical pretreatment methods for improving saccharification of cotton stalks, Bioresource Technology, 2007, pp. 3000-3011, vol. 98.

(Continued)

*Primary Examiner* — Manjunath Rao
*Assistant Examiner* — William W Moore (57) ABSTRACT

Methods for obtaining concentrated sugar solution from polysaccharide enriched biomass by contacting biomass with water and at least one nucleophilic base to produce a polysaccharide enriched biomass comprising a solid fraction and a liquid fraction and then contacting the solid fraction with saccharification enzyme consortium to produce a saccharification product comprising at least about 7 percent by weight sugars in 24 hours. The methods include optionally adding at least one additive selected from the group consisting of polyethylene glycols, fatty acid esters, fatty acid ethoxylates, nonionic surfactants derived from polyethoxylated sorbitan and a fatty acid, sodium lauriminodipropionate, sodium cocoamphoacetate, sodium tridecyl ether sulfate and a combination of these, such that enzyme loading of the saccharification enzyme consortium can be reduced.

7 Claims, 2 Drawing Sheets

(56) References Cited

U.S. PATENT DOCUMENTS

| | | | | |
|---|---|---|---|---|
| 6,752,902 | B2 | 6/2004 | Heikkilaet et al. | |
| 7,354,743 | B2 | 4/2008 | Vlasenko et al. | |
| 7,807,021 | B2* | 10/2010 | Blackstone et al. | 162/80 |
| 2004/0231060 | A1 | 11/2004 | Burdette et al. | |
| 2007/0031918 | A1* | 2/2007 | Dunson et al. | 435/41 |
| 2008/0274509 | A1* | 11/2008 | Filho et al. | 435/72 |
| 2009/0317871 | A1* | 12/2009 | Kim et al. | 435/71.2 |
| 2010/0035318 | A1 | 2/2010 | MeloSantanna et al. | |
| 2010/0124770 | A1* | 5/2010 | Sabesan et al. | 435/101 |
| 2010/0143974 | A1* | 6/2010 | Chung et al. | 435/72 |

OTHER PUBLICATIONS

Teixeira, Lincoln C. et al., Alkaline and Peracetic Acid Pretreatments of Biomass for Ethanol Production, Applied Biochemistry and Biotechnology, 1999, pp. 19-34, vol. 77-79.

Jorgensen, Henning et al., Liquefaction of Lignocellulose at High-Solids Concentrations, Biotechnology and Bioengineering, Apr. 1, 2007, pp. 862-870, vol. 96, No. 5.

Qiabi, A. et al., Comparative studies of hemicellulose hydrolysis processes: application to various lignocellulosic wastes, Industrial Crops and Products, 1994, pp. 95-102, vol. 3, Elsevier Science B.V.

Al-Ani, F. et al., Effect of Chemical Pretreatments on the Fermentation and Ultimate Digestibility of Bagasse by *Phanerochaete chryosporium*, J. Sci. Food Agric., 1998, pp. 19-28, vol. 42, Society of Chemical Industry.

Akhtar, Muhammad Saleem et al., Saccharification of Lignocellulosic Materials by the Cellulases of *Bacillus subtilis*, International Journal of Agriculture & Biology, 2001, pp. 199-202, vol. 3, No. 2.

Archibald, J. G., The Effect of Sodium Hydroxid on the Composition, Digestibility, and Feeding Value of Grain Hulls and Other Fibrous Material, Journal of Agricultural Research, Feb. 2, 1924, pp. 245-265, vol. 27, No. 5.

Brief Description of Electroep's Mild-Pretreatment Process for Cellulosic Biofuels, Oct. 23, 2008, Electrostep, Inc., Corvallis, Oregon.

Borjesson, Johan et al., Enhanced enzymatic conversion of softwood lignocellulose by poly(ethylene glycol) addition, Enzyme and Microbial Technology, 2007, pp. 754-762, vol. 40, Elsevier Inc.

Singh, A. et al., Saccharification of cellulosic substrates by *Aspergillus niger* cellulase, World Journal of Microbiology and Biotechnology, 1990, pp. 333-336, vol. 6, Rapid Communications of Oxford Ltd.

Tewari, Harmesh K. et al., Role of Pretreatments on Enzymatic Hydrolysis of Agricultural Residues for Reducing Sugar Production, Journal of Chemical Technology and Biotechnology, 1987, pp. 153-165, vol. 38, No. 38, Society of Chemical Industry.

Hsu, Wen-Hui et al., A new alkali process for the treatment of agricultural byproducts, Shipin Gongye, 1978, vol. 10, No. 1, Food. Ind. Res. Dev. Inst., Hsinchu, Taiwan (Abstract attached).

\* cited by examiner

PROCESS FOR PRODUCING A CONCENTRATED SUGAR SOLUTION BY ENZYMATIC SACCHARIFICATION OF POLYSACCHARIDE ENRICHED BIOMASS

CROSS-REFERENCE TO RELATED APPLICATIONS

This application claims benefit of priority from Provisional Application No. 61/116382 filed Nov. 20, 2008, and from Provisional Application No. 61/116386 filed Nov. 20, 2008. This application hereby incorporates by reference Provisional Application Nos. 61/116382 and 61/116386 in their entirety.

FIELD OF THE INVENTION

Methods for treating biomass to obtain concentrated sugar solutions are provided. Specifically, polysaccharide enriched biomass is obtained by the pretreatment of biomass with at least one nucleophilic base in a manner which retains the glucan/xylan weight ratio of the untreated biomass. Concentrated sugar solutions are obtained by enzymatic saccharification of the polysaccharide enriched biomass, optionally in the presence of at least one additive.

BACKGROUND

Cellulosic and lignocellulosic feedstocks and wastes, such as agricultural residues, wood, forestry wastes, sludge from paper manufacture, and municipal and industrial solid wastes, provide a potentially large renewable feedstock for the production of valuable products such as fuels and other chemicals. Cellulosic and lignocellulosic feedstocks and wastes, composed of carbohydrate polymers comprising cellulose, hemicellulose, and lignin are generally treated by a variety of chemical, mechanical and enzymatic means to release primarily hexose and pentose sugars, which can then be fermented to useful products.

Pretreatment methods are used to make the carbohydrate polymers of cellulosic and lignocellulosic materials more readily available to saccharification enzymes. Standard pretreatment methods have historically utilized primarily strong acids at high temperatures; however due to high energy costs, high equipment costs, high pretreatment catalyst recovery costs and incompatibility with saccharification enzymes, alternative methods are being developed, such as enzymatic pretreatment, or the use of acid or base at milder temperatures where decreased hydrolysis of biomass carbohydrate polymers occurs during pretreatment, requiring improved enzyme systems to saccharify both cellulose and hemicellulose.

Teixeira, L., et al. (Appl. Biochem. and Biotech. (1999) 77-79:19-34) disclosed a series of biomass pretreatments using stoichiometric amounts of sodium hydroxide and ammonium hydroxide, with very low biomass concentration. The ratio of solution to biomass is 14:1.

Elshafei, A. et al. (Bioresource Tech. (1991) 35:73-80) examined the pretreatment of corn stover utilizing NaOH. Kim, T. and Y. Lee (Bioresource Technology (2005) 96:2007-2013) report the use of high amounts of aqueous ammonia for the pretreatment of corn stover.

Int'l. Pat. App. Pub. No. WO2004/081185 discusses methods for hydrolyzing lignocellulose, comprising contacting the lignocellulose with a chemical; the chemical may be a base, such as sodium carbonate or potassium hydroxide, at a pH of about 9 to about 14, under moderate conditions of temperature, pressure and pH.

U.S. Pat. Nos. 5,916,780 and 6,090,595, describe a pretreatment process wherein a specified ratio of arabinoxylan to total nonstarch polysaccharides (AX/NSP) is assessed and used to select the feedstock.

U.S. Pat. No. 7,354,743 discloses methods for degrading a lignocellulosic material, comprising treating the lignocellulosic material with an effective amount of one or more cellulolytic enzymes in the presence of at least one surfactant; the presence of the surfactant increases the degradation of lignocellulosic material compared to the absence of the surfactant.

Borjesson, J. et al. (Enzyme and Microbial. Technology (2007) 40:754-762) focused on the enzymatic hydrolysis of the softwood substrate spruce lignocellulose and aimed to give further understanding of the mechanism behind the enhancing effect on the conversion by addition of ethylene oxide based surfactants and polymers. No effect of PEG was seen on a delignified substrate.

Int'l. Pat. App. Pub. No. WO2008134037 added surfactants in the pretreatment step to enhance the removal of lignin in corn stover biomass in an effort to increase the digestibility of the delignified biomass. However, not considered was a reduction in enzyme loading nor reported was a saccharification product comprising at least about 7 percent by weight sugars in a 24 hour period after contact with an enzyme consortium.

Most pretreatments such as the ones described above either result in a pretreated biomass depleted of lignin and hemicellulose or the partial depletion of hemicellulose with retention of most of the lignin. Therefore a method is needed to selectively remove only lignin without significant loss of either hemicellulose or cellulose from the biomass, as these constitute the source of sugars for fermentation. Thus, none of these references relates to the unpredicted mechanism recited herein: retaining hemicellulose or cellulose in the biomass such that the saccharification product comprises at least about 7 percent by weight sugars in a 24 hour period after contact with an enzyme consortium.

In order to be economically competitive, a commercial process for the production of sugars from a renewable resource biomass requires the hydrolysis of carbohydrates in lignocellulosic biomass to provide high yields of sugars at high concentrations using low amounts of chemicals.

SUMMARY

Described herein are methods to produce a concentrated sugar solution from polysaccharide enriched biomass containing both hemicellulose and cellulose. The described methods involve a pretreatment step wherein biomass is contacted with water and at least one nucleophilic base, with subsequent change in pH that may range about 12.5-13.0 to about 9.5-10. During pretreatment, the lignin is solubilized and the glucan/xylan weight ratio in the insoluble biomass is largely retained, compared to that for untreated biomass. The solid fraction of the resulting polysaccharide enriched biomass is contacted as an aqueous suspension with a saccharification enzyme consortium, and optionally with at least one additive, to produce a saccharification product comprising at least about 7 percent by weight sugars in 24 hours.

One method described herein is a method of producing a concentrated sugar solution from biomass, the method comprising:

a) delignifying biomass comprising the substeps of
   i) contacting with water and at least one nucleophilic base, a biomass comprising lignin and having a glucan/xylan weight ratio $G_1/X_1$ to form a biomass slurry having a pH of about 12.5 to about 13.0; and ii) maintaining the biomass slurry under reaction conditions such that the slurry attains a pH of about 9.5 to about 10.0 and has a a glucan/xylan weight ratio $G_2/X_2$ within about 15% of the value of $G_1/X_1$, and wherein the slurry comprises a lignin-containing liquid fraction and a solid fraction comprising a polysaccharide enriched biomass;

wherein $G_1$ and $G_2$ are grams of glucan per 100 grams of biomass and biomass slurry respectively, and $X_1$ and $X_2$ are grams of xylan per 100 grams of biomass and biomass slurry respectively; and b) contacting with a saccharification enzyme consortium an aqueous suspension of at least a portion of the solid fraction of the polysaccharide enriched biomass, the solid fraction of the polysaccharide enriched biomass being 13 weight percent to about 30 weight percent of the aqueous suspension, at reaction conditions sufficient to produce a saccharification product comprising at least about 7 percent by weight sugars, based on the total weight of the saccharification product, in 24 hours of contact with the saccharification enzyme consortium.

In the above method described herein, the at least one nucleophilic base may comprise a water soluble metal hydroxide, optionally in combination with a metal carbonate or an organic hydroxide. The water soluble metal hydroxide is selected from the group consisting of sodium hydroxide or potassium hydroxide and the metal carbonate or the organic hydroxide is selected from the group consisting of sodium carbonate, potassium carbonate, ammonium hydroxides, and alkyl substituted ammonium hydroxide. The reaction conditions to produce a polysaccharide enriched biomass include a temperature from about 20° C. to about 110° C. and a reaction time from about 4 hours to about 30 days. The value of $G_2/X_2$ may be within 10% of the value of $G_1/X_1$.

The composition of the solid fraction of the polysaccharide enriched biomass solid fraction, on a dry weight basis, may be greater than about 85% polysaccharide.

Another method described herein comprises:
a) providing biomass having undergone a delignification process to become a delignified biomass and comprising greater than about 85 percent polysaccharides on a dry weight basis;
b) contacting with a saccharification enzyme consortium an aqueous suspension of the delignified biomass, the concentration of the delignified biomass in the aqueous suspension being from about 13 weight percent to about 30 weight percent, at reaction conditions sufficient to produce a saccharification product comprising at least about 7 percent by weight sugars, based on the total weight of the saccharification product, in 24 hours of contact with the saccharification enzyme consortium.

In any method described herein, at least one additive may be added, such that enzyme loading of the saccharification enzyme consortium is reduced relative to enzyme loading of the saccharification enzyme consortium when none of the additives is added. The additive is from about 0.1 weight percent to about 5 weight percent, based on the weight of the isolated polysaccharide enriched biomass solid fraction in the aqueous suspension. The additive is selected from the group consisting of polyethylene glycols, fatty acid esters, fatty acid ethoxylates, nonionic surfactants derived from polyethoxylated sorbitan and a fatty acid, sodium lauriminodipropionate, sodium cocoamphoacetate, sodium tridecyl ether sulfate, and a combination of these. The polyethylene glycol may have a molecular weight between 500 to 50,000 Daltons. The fatty acid ester may be selected from the group consisting of methyl esters of $C_{12}$ to $C_{30}$ fatty acid esters.

Another method described herein is a method for delignifying a biomass to produce a polysaccharide enriched biomass, the process comprising:
a) contacting with water and at least one nucleophilic base, a biomass comprising lignin and having a glucan/xylan weight ratio $G_1/X_1$ to form a biomass slurry having a pH of about 12.5 to about 13.0; and
b) maintaining the biomass slurry under reaction conditions such that the slurry attains a pH of about 9.5 to about 10.0 and has a a glucan/xylan weight ratio $G_2/X_2$ within about 15% of the value of $G_1/X_1$, and wherein the slurry comprises a lignin-containing liquid fraction and a solid fraction comprising a polysaccharide enriched biomass;

wherein $G_1$ and $G_2$ are grams of glucan per 100 grams of biomass and biomass slurry respectively, and $X_1$ and $X_2$ are grams of xylan per 100 grams of biomass and biomass slurry respectively.

Also described is a polysaccharide enriched biomass produced by the process described above.

BRIEF DESCRIPTION OF THE FIGURES

The methods described herein are described with reference to the following figures.

DETAILED DESCRIPTION OF THE INVENTION

Definitions

The methods described herein are described with reference to the following terms.

As used herein, where the indefinite article "a" or "an" is used with respect to a statement or description of the presence of a step in a process of this invention, it is to be understood, unless the statement or description explicitly provides to the contrary, that the use of such indefinite article does not limit the presence of the step in the process to one in number.

As used herein, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

The term "invention" or "present invention" as used herein is a non-limiting term and is not intended to refer to any single variation of the particular invention but encompasses all possible variations described in the specification and recited in the claims.

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. The term "about" may mean within 10% of the reported numerical value, preferably within 5% of the reported numerical value.

As used herein, the term "biomass" refers to any cellulosic or lignocelulosic material and includes materials comprising cellulose, and optionally further comprising hemicellulose, lignin, starch, oligosaccharides and/or monosaccharides. Biomass may also comprise additional components, such as protein and/or lipid. Biomass may be derived from a single source, or biomass can comprise a mixture derived from more than one source; for example, biomass could comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste or a combination thereof. Examples of biomass include, but are not limited to, corn grain, corn cobs, crop residues such as corn husks, corn stover, grasses, wheat, wheat straw, barley, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers, and animal manure or a combination thereof. Biomass that is useful for the invention may include biomass that has a relatively high carbohydrate value, is relatively dense, and/or is relatively easy to collect, transport, store and/or handle. In one embodiment of the invention, biomass that is useful includes corn cobs, corn stover, sawdust, and sugar cane bagasse.

As used herein, the term "lignocelulosic" refers to a composition comprising both lignin and cellulose. Lignocelulosic material may also comprise hemicellulose.

As used herein, the term "cellulosic" refers to a composition comprising cellulose.

As used herein, by "dry weight" of biomass is meant the weight of the biomass having all or essentially all water removed. Dry weight is typically measured according to American Society for Testing and Materials (ASTM) Standard E1756-01 (Standard Test Method for Determination of Total Solids in Biomass) or Technical Association of the Pulp and Paper Industry, Inc. (TAPPI) Standard T-412 om-02 (Moisture in Pulp, Paper and Paperboard).

As used herein, the terms "target chemical" and "target product" are interchangeable and refer to a chemical, fuel, or chemical building block produced by fermentation. Chemical or product is used in a broad sense and includes molecules such as proteins, including, for example, peptides, enzymes, and antibodies. Also contemplated within the definition of target product are ethanol and butanol.

As used herein, the term "saccharification" refers to the hydrolysis of polysaccharides to their constituent monomers and/or oligomers.

As used herein, the term "polysaccharide enriched biomass" means biomass that has been subjected to pretreatment prior to saccharification such that the noncarbohydrate component of the biomass is significantly reduced.

As used herein, "readily saccharifiable biomass" means biomass that is carbohydrate-enriched and made more amenable to hydrolysis by cellulolytic or hemi-cellulolytic enzymes for producing monomeric and oligomeric sugars. The term "readily saccharifiable biomass" as used herein is interchangeable with the term "solid fraction of the polysaccharide enriched biomass".

As used herein, the term "carbohydrate-enriched" as used herein refers to the biomass produced by the process treatments described herein. The terms polysaccharide enriched and carbohydrate-enriched are interchangeable. in one embodiment the readily saccharifiable carbohydrate-enriched biomass produced by the processes described herein have a carbohydrate concentration of greater than or equal to about 85% of the biomass carbohydrate as compared to biomass prior to pretreating as described herein while removing 75% or greater of the biomass lignin.

As used herein, the term "loading of the enzyme consortium" and "enzyme loading" are interchangeable and refer to a ratio of the amount total weight of protein in the enzyme consortium relative to the weight of polysaccharide enriched biomass.

As used herein, the terms "delignification" refers to any process by which lignin is either partly, mostly or wholly removed from cellulosic materials. Generally, this process is by means of chemical treatment. The residue that remains consists of cellulose, hemicelluloses, and other carbohydrate materials. Any residue having undergone a delignification is described herein as "delignified". As used herein, "lignin" refers generally to a polymer found extensively in the cell walls of all woody plants.

As used herein, the term "cellulase" refers to polysaccharide-hydrolyzing enzymes that can exhibit an activity, such as cellulose degradation, that may be several enzymes or a group of enzymes having different substrate specificities. Thus, a cellulase from a microorganism may comprise a group of enzymes, all of which may contribute to the cellulose-degrading activity.

As used herein, the terms "nucleophile" and "nucleophilic base" refer to a Lewis base (as that term is used in the art) that is a reagent that forms a chemical bond to its reaction partner, the electrophile, by donating both bonding electrons. Most bases are also nucleophiles. (See for example *Organic Chemistry, 7th Edition*, Morrison, Robert Thornton; Boyd, Robert N., (1998) Publisher: (Prentice Hall, Englewood Cliffs, N.J.). For example, in the methods described herein, the nucleophile NaOH reacts and forms chemical bonds with lignin and its components.

Pretreatment (Delignification)

In the methods described herein, biomass is contacted with water and at least one nucleophilic base to form a biomass slurry having an initial pH of about 12.5 to about 13.0. The biomass has a glucan/xylan weight ratio $G_1/X_1$, where $G_1$ is the grams of glucan per 100 grams of biomass and $X_1$ is the grams of xylan per 100 grams of biomass. Glucan and xylan content of biomass can be determined by methods known in the art. The source of the biomass is not determinative of the invention and the biomass may be from any source.

Once processed the biomass slurry is maintained at a temperature and for a reaction time sufficient to produce a polysaccharide enriched biomass having a glucan/xylan weight ratio $G_2/X_2$, where $G_2$ is the grams of glucan per 100 grams of polysaccharide enriched biomass and $X_2$ is the grams of xylan per 100 grams of polysaccharide enriched biomass. In contrast to other pretreatment methods, the polysaccharide enriched biomass is produced without selective loss of xylan, as evidenced by a comparison of the values of the ratios $G_2/X_2$ and $G_1/X_1$. Similarity of the numerical values for the glucan/xylan weight ratios of the treated and the untreated biomass indicate that both glucan and xylan are retained in about the same relative amounts in the polysaccharide enriched biomass as were present in the biomass before pretreatment. In one of the described methods, the value of $G_2/X_2$ is within about 15% of the value of $G_1/X_1$. In another, the value of $G_2/X_2$ is within about 10% of the value of $G_1/X_1$. Avoiding preferential loss of xylan during the pretreatment step provides higher xylose yield after saccharification and contributes to improved sugar yields overall and higher sugar concentrations.

The pretreated biomass is referred to as "polysaccharide enriched biomass" or "carbohydrate-enriched biomass" because the pretreatment described above, and in more detail below, solubilizes the lignin contained in the biomass. The glucan and xylan remain insoluble. Physical separation of the lignin-containing liquid fraction from the solid fraction removes lignin and provides solid polysaccharide enriched biomass.

Delignifying biomass prior to enzymatic hydrolysis (saccharification) is advantageous as lignin can bind non-specifically to saccharification enzymes. Removal of lignin before saccharification enables the use of lower enzyme loadings, which provides cost savings with regard to enzyme usage. Removing lignin before saccharification can also improve saccharification rate, titer, and yield. Furthermore, as lignin can contribute to increased viscosity of biomass and biomass slurry, removal of lignin can provide reduced viscosity of biomass and slurries containing biomass, thereby enabling very high loading, for example, greater than about 20 percent, of the biomass in order to produce concentrated sugar syrup.

The biomass may be used directly as obtained from the source, or energy may be applied to the biomass to reduce the size, increase the exposed surface area, and/or increase the availability of cellulose, hemicellulose, and/or oligosaccharides present in the biomass to the nucleophilic base and to saccharification enzymes and/or additive used in the saccharification step. Energy means useful for reducing the size, increasing the exposed surface area, and/or increasing the availability of cellulose, hemicellulose, and/or oligosaccharides present in the biomass include, but are not limited to, milling, crushing, grinding, shredding, chopping, disc refining, ultrasound, and microwave. This application of energy may occur before or during pretreatment, before and during saccharification, or any combination thereof.

In general, it is often required to mill the biomass before and/or after pretreatments in order to reduce the particle size and to produce high surface area and porous particles for effective enzymatic saccharification. In the current invention, we unexpectedly find that this energy intensive milling process can be avoided, as the nucleophilic base treatment under selected conditions results in chemical milling to provide delignified biomass of substantially reduced particle size.

The biomass is contacted with water sufficient to wet the entire biomass and at least one nucleophilic base comprising a water soluble metal hydroxide, such as sodium hydroxide or potassium hydroxide. The water soluble metal hydroxide may be used alone or in combination with a metal carbonate, such as sodium carbonate or potassium carbonate, or an organic hydroxide, such as ammonium or alkyl substituted ammonium hydroxides. The nucleophilic base is combined as an aqueous solution or as a solid with the biomass and water to form biomass slurry having an initial pH of about 12.5 to about 13.0. As the delignification proceeds, some of the base is consumed and the pH of the biomass slurry is reduced to a range of about 9.5 to about 10.0. A sufficient concentration of base should be used such that the pH does not drop lower, which would result in insufficient delignification. The extent of delignification can depend at least in part on the choice of reaction conditions and the type of biomass used. For example, in the case of corn cob, about 8 weight percent of NaOH relative the weight of the corn cob has been found to provide optimum delignification. At least about 70 percent of the lignin in the provided biomass may be delignified in the isolated polysaccharide enriched biomass. At least about 80 percent of the lignin in the provided biomass may be delignified in the isolated polysaccharide enriched biomass. At least about 90 percent of the lignin may be delignified in the isolated polysaccharide enriched biomass.

The amount of water in the biomass slurry may be from about 25 weight percent to about 90 weight percent, for example from about 50 weight percent to about 90 weight percent, or from about 75 weight percent to about 90 weight percent based on the combined weight of the biomass, the water, and the nucleophilic base. The water in the biomass slurry refers to the total water from all sources and includes any water contained in or on the biomass, water contained in an aqueous solution of the nucleophilic base, and water added separately.

In the methods described herein, the dry weight of biomass in the biomass slurry may be at an initial concentration from about 10 weight percent to about 75 weight percent, or for example from about 10 weight percent to about 50 weight percent, or for example from about 10 weight percent to about 25 weight percent, based on the combined weight of the biomass, the water, and the nucleophilic base. The biomass concentration may be maximized to the extent possible to minimize the volume of the reaction vessel. The high biomass concentration also reduces the total volume of pretreatment material, making the process more economical. From a practical viewpoint, high ratios of the weight of biomass to the weight of the basic solution may be limited by the ability to provide sufficient mixing, or intimate contact, for pretreatment to occur at a practical rate.

The biomass slurry is maintained at a temperature of from about 20° C. to about 110° C., for example from about 80° C. to about 110° C.

The contacting of the biomass with water and at least one nucleophilic base is carried out for a period time from about 4 hours to about 30 days, for example from about 4 hours to about 1 day. Longer periods of pretreatment are possible, however a shorter period of time may be preferable for practical, economic reasons. Typically a period of contact may be about 24 hours or less and may be determined by the time required for the pH of the biomass slurry to drop from a range of about 12.5 to 13.0 to a range of about 9.5 to 10.0.

The delignification of biomass with water and at least one nucleophilic base may be performed at a relatively high temperature for a relatively short period of time, for example at from about 90° C. to about 100° C. for about 24 hours to about 16 hours. Alternatively, the biomass-nucleophilic base contacting process may be performed at a lower temperature for a longer period of time, for example from about 50° C. to about 80° C. for about 140 hours to about 100 hours. Moreover, the biomass-acid contacting process may be performed at room temperature (approximately 22-25° C.) for a period of time up to about 300 hours. Other temperature and time combinations intermediate to these may also be used.

For the contacting of the biomass with water and at least one nucleophilic base, the temperature, reaction time, base concentration, weight percent of total water, the biomass concentration, the biomass type, and the biomass particle size are related; thus these variables may be adjusted as necessary to obtain sufficient delignification rate in a controllable manner and to obtain an optimal product for saccharification to sugars.

The pretreatment may be performed in any suitable vessel, such as a batch reactor a continuous reactor. The suitable vessel may be equipped with a means, such as impellers, for agitating the biomass/acid mixture. Reactor design is discussed in Lin, K.-H., and Van Ness, H. C. (in Perry, R. H. and Chilton, C. H. (eds), Chemical Engineer's Handbook, $5^{th}$ Edition (1973) Chapter 4, McGraw-Hill, NY). The pretreatment may be carried out as a batch process, or as a continuous process. Alternatively, the biomass, water and nucleophilic base may be combined in one vessel, then transferred to another reactor. Also biomass may be pretreated in one vessel, then further processed in another reactor.

In order to obtain sufficient quantities of sugars from biomass, the biomass may be pretreated with water and at least one nucleophilic base either once or several times. Likewise, a saccharification reaction may be performed one or more times. Both pretreatment and saccharification processes may be repeated if desired to obtain higher yields of sugars. To assess performance of the pretreatment and saccharification processes, separately or together, the theoretical yield of sugars derivable from the starting biomass may be determined and compared to the measured yields.

Saccharification

Following pretreatment of the provided biomass with water and at least one nucleophilic base, the polysaccharide enriched biomass comprises a mixture of nucleophilic base, water, partially degraded biomass, lignin, polysaccharides, and monosaccharides. The mixture comprises a solid (insoluble) fraction and a liquid (soluble) fraction. The solid fraction comprises biomass in which the non-carbohydrate component has been significantly reduced. The liquid fraction is composed of lignin and its fragments as its metal salt, along with the excess base and salts related to the nucleophilic base. Prior to saccharification, at least a portion of the solid fraction of the polysaccharide enriched biomass may be isolated in order to physically separate it from the lignin-containing liquid fraction. Isolation of as much of the solid fraction as possible is advantageous, as this allows higher yield of sugars to be obtained after saccharification. In the methods described herein, the composition of the isolated solid fraction of the polysaccharide enriched biomass, on a dry weight basis, is greater than about 75% polysaccharide. The composition of the isolated solid fraction of the polysaccharide enriched biomass, on a dry weight basis, may be greater than about 80% polysaccharide or greater than about 85% polysaccharide or greater than about 90% polysaccharide.

Methods for separating the solid fraction from the liquid fraction include, but are not limited to, decantation, filtration, and centrifugation. Methods of filtration include, for example, belt filtration, vacuum filtration, and pressure filtration. Optionally, at least a portion of the solid fraction may be recycled to the pretreatment reactor. The solid fraction may optionally be washed with an aqueous solvent (e.g., water) to remove adsorbed lignin prior to being recycled to the pretreatment reactor. The solid fraction may then be re-subjected to additional treatment with at least one nucleophilic base as described above for pretreatment, followed by saccharification with a saccharification enzyme consortium.

The liquid fraction may optionally be used as an energy source, or some of the desirable components contained in it may be isolated for additional uses.

In the methods described herein, an aqueous suspension of the solid fraction of the polysaccharide enriched biomass is contacted with a saccharification enzyme consortium, and optionally with at least one additive, at a pH and a temperature sufficient to produce a saccharification product comprising at least about 7 percent by weight sugars in 24 hours of contact with the saccharification enzyme consortium. The concentration of the solid fraction of the polysaccharide enriched biomass in the aqueous suspension may be from about 13 weight percent to about 30 weight percent, for example, from about 21 weight percent to about 30 weight percent, or for example, from about 15 weight percent to about 25 weight percent. The at least one additive is selected from the group consisting of polyethylene glycols, fatty acid esters, fatty acid ethoxylates, nonionic surfactants derived from polyethoxylated sorbitan and a fatty acid, and a combination of these.

Alternatively, delignified biomass comprising greater than about 85 percent polysaccharides on a dry weight basis can be used in place of the isolated solid fraction of polysaccharide enriched biomass obtained as described above. This delignified biomass can be obtained by an alternative method.

Prior to saccharification, the aqueous suspension of the solid fraction of the polysaccharide enriched biomass may be treated to alter the pH, composition or temperature such that the enzymes of the saccharification enzyme consortium will be active. The pH may be altered through the addition of acids in solid or liquid form. Alternatively, carbon dioxide ($CO_2$), which may be recovered from fermentation, may be utilized to lower the pH. For example, $CO_2$ may be collected from a fermenter and fed, such as by bubbling, into the aqueous suspension of the isolated polysaccharide enriched biomass while monitoring the pH, until the desired pH is achieved. The temperature may be brought to a temperature that is compatible with saccharification enzyme activity, as noted below. Any cofactors required for activity of enzymes used in saccharification may be added.

At least a portion of the isolated solid fraction of the polysaccharide enriched biomass is then further hydrolyzed in the presence of a saccharification enzyme consortium to release oligosaccharides and/or monosaccharides in a hydrolyzate. Saccharification enzymes and methods for biomass treatment are reviewed in Lynd, L. R., et al. (Microbiol. Mol. Biol. Rev. (2002) 66:506-577).

The saccharification enzyme consortium comprises one or more enzymes selected primarily, but not exclusively, from the group "glycosidases" which hydrolyze the ether linkages of di-, oligo-, and polysaccharides and are found in the enzyme classification EC 3.2.1.x (Enzyme Nomenclature 1992, Academic Press, San Diego, Calif. with Supplement 1 (1993), Supplement 2 (1994), Supplement 3 (1995, Supplement 4 (1997) and Supplement 5 [in Eur. J. Biochem. (1994) 223:1-5, Eur. J. Biochem. (1995) 232:1-6, Eur. J. Biochem. (1996) 237:1-5, Eur. J. Biochem. (1997) 250:1-6, and Eur. J. Biochem. (1999) 264:610-650, respectively]) of the general group "hydrolases" (EC 3.). Glycosidases useful in the present method can be categorized by the biomass component that they hydrolyze. Glycosidases useful for the present method include cellulose-hydrolyzing glycosidases (for example, cellulases, endoglucanases, exoglucanases, cellobiohydrolases, β-glucosidases), hemicellulose-hydrolyzing glycosidases (for example, xylanases, endoxylanases, exoxylanases, β-xylosidases, arabinoxylanases, mannases, galactases, pectinases, glucuronidases), and starch-hydrolyzing glycosidases (for example, amylases, α-amylases, β-amylases, glucoamylases, α-glucosidases, isoamylases). In addition, it may be useful to add other activities to the saccharification enzyme consortium such as peptidases (EC 3.4.x.y), lipases (EC 3.1.1.x and 3.1.4.x), ligninases (EC 1.11.1.x), and feruloyl esterases (EC 3.1.1.73) to help release polysaccharides from other components of the biomass. It is well known in the art that microorganisms that produce polysaccharide-hydrolyzing enzymes often exhibit an activity, such as cellulose degradation, that is catalyzed by several enzymes or a group of enzymes having different substrate specificities. Thus, a "cellulase" from a microorganism may comprise a group of enzymes, all of which may contribute to the cellulose-degrading activity. Commercial or non-commercial enzyme preparations, such as cellulase, may comprise numerous enzymes depending on the purification scheme utilized to obtain the enzyme. Thus, the saccharification enzyme consortium of the present method may comprise enzyme activity, such as "cellulase", however it is recognized that this activity may be catalyzed by more than one enzyme.

Saccharification enzymes may be obtained commercially, such as Spezyme® CP cellulase (Genencor International, Rochester, N.Y.) and Multifect® xylanase (Genencor). In addition, saccharification enzymes may be produced biologically, including using recombinant microorganisms.

Preferably the saccharification reaction is performed at or near the temperature and pH optima for the saccharification enzymes. The temperature optimum used with the saccharification enzyme consortium in the present method may range from about 15° C. to about 100° C. The temperature optimum may range from about 20° C. to about 80° C., or from about 30° C. to about 60° C., or from about 45° C. to about 55° C. The pH optimum may range from about 4 to about 6 or from about 4.5 to about 5.5 or from about 4.5 to about 5.0.

The saccharification may be performed for a time of about several minutes to about 168 hours, for example from about several minutes to about 48 hours. The time for the reaction will depend on enzyme concentration and specific activity, as well as the substrate used and the environmental conditions, such as temperature and pH. One skilled in the art can readily determine optimal conditions of temperature, pH and time to be used with a particular substrate and saccharification enzyme(s) consortium. These variables may be adjusted as necessary to obtain an optimal saccharification product for use in fermentation.

The saccharification may be performed batch-wise or as a continuous process. The saccharification may also be performed in one step, or in a number of steps. For example, different enzymes required for saccharification may exhibit different pH or temperature optima. A primary treatment can be performed with enzyme(s) at one temperature and pH, followed by secondary or tertiary (or more) treatments with different enzyme(s) at different temperatures and/or pH. In addition, treatment with enzymes in sequential steps may be at the same pH and/or temperature, or different pHs and temperatures, such as using hemicellulases stable and more active at higher pHs and temperatures followed by cellulases that are active at lower pHs and temperatures.

At least one additive may be present in the contacting of the aqueous suspension of the solid fraction of the polysaccharide enriched biomass with the saccharification enzyme consortium. The additive is selected from the group consisting of polyethylene glycols, fatty acid esters, fatty acid ethoxylates, nonionic surfactants derived from polyethoxylated sorbitan and a fatty acid, sodium lauriminodipropionate, sodium cocoamphoacetate, and sodium tridecyl ether sulfate, and a combination of these. Examples of suitable additives include, but are not limited to, polyethylene glycol having molecular weight from about 500 to about 50,000 Daltons and commercial vegetable oil based surfactants such as fatty acid esters. The fatty acid ester may be selected from the group consisting of methyl esters of $C_{12}$ to $C_{30}$ fatty acid esters. The fatty acid ethoxylate may be selected from the group consisting of ethoxylates of $C_{12}$ to $C_{30}$ fatty acids. Also suitable are non-ionic surfactants derived from polyethoxylated sorbitan and a fatty acid such as lauric acid or oleic acid, for example polysorbates. A combination of surfactants may also be used. Examples of commercially available additives useful in the present invention are shown in Table 9. The concentration of the additive may be from about 0.1 weight percent to about 5.0 weight percent or from about 0.25 weight percent to about 3.0 weight percent, based on the weight of the solid fraction of the polysaccharide enriched biomass in the aqueous suspension.

In these methods, the use of an additive in conjunction with a low enzyme loading enhances the saccharification yield, as compared to the case where no additive is used. Use of an additive in conjunction with a low enzyme loading also leads to higher saccharification enhancement as compared to the case where higher loadings of enzyme are used with an additive. The loading of the enzyme consortium is such that it is sufficient for the additive to be effective. Reducing the loading of the enzyme consortium reduces process cost and improves overall process economics.

The saccharification product comprises sugars, wherein the sugars comprise at least one sugar monomer selected from the group consisting of glucose, arabinose, xylose, mannose, galactose, and a combination thereof. The saccharification product may comprise: at least about 7 percent by weight sugars, based on the total weight of the saccharification product, in 24 hours of contact with the saccharification enzyme consortium; or at least about 18 percent by weight sugars in 168 hours of contact with the saccharification enzyme consortium. The concentration of the solid fraction of the polysaccharide enriched biomass in the aqueous suspension for saccharification may be from about 21 weight percent to about 30 weight percent, and the saccharification product may comprise sugars corresponding to at least a 65% saccharification yield, based on the sum of glucan and xylan in the polysaccharide enriched biomass.

The saccharification reaction may be performed in any suitable vessel, such as a batch reactor a continuous reactor. The suitable vessel may be equipped with a means, such as impellers, for agitating the biomass/acid mixture. Reactor design is discussed in Lin, K.-H., and Van Ness, H. C. (in Perry, R. H. and Chilton, C. H. (eds), Chemical Engineer's Handbook, 5$^{th}$ Edition (1973) Chapter 4, McGraw-Hill, NY).

The degree of solubilization of sugars from biomass following saccharification may be monitored by measuring the release of monosaccharides and oligosaccharides. Methods to measure monosaccharides and oligosaccharides are well known in the art. For example, the concentration of reducing sugars can be determined using the 1,3-dinitrosalicylic (DNS) acid assay (Miller, G. L., Anal. Chem. (1959) 31:426-

428). Alternatively, sugars can be measured by HPLC using an appropriate column as described herein in the General Methods section.

Fermentation to Target Products

The readily saccharifiable biomass produced by the present methods may be hydrolyzed by enzymes as described above to produce fermentable sugars which then may be fermented into a target product. "Fermentation" refers to any fermentation process or any process comprising a fermentation step. Target products include, without limitation alcohols (e.g., arabinitol, butanol, ethanol, glycerol, methanol, 1,3-propanediol, sorbitol, and xylitol); organic acids (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, propionic acid, succinic acid, and xylonic acid);

ketones (e.g., acetone); amino acids (e.g., aspartic acid, glutamic acid, glycine, lysine, serine, and threonine); gases (e.g., methane, hydrogen ($H_2$), carbon dioxide ($CO_2$), and carbon monoxide (CO)).

Fermentation processes also include processes used in the consumable alcohol industry (e.g., beer and wine), dairy industry (e.g., fermented dairy products), leather industry, and tobacco industry.

Further to the above, the sugars produced from saccharifying the pretreated biomass as described herein may be used to produce in general, organic products, chemicals, fuels, commodity and specialty chemicals such as xylose, acetone, acetate, glycine, lysine, organic acids (e.g., lactic acid), 1,3-propanediol, butanediol, glycerol, ethylene glycol, furfural, polyhydroxyalkanoates, cis, cis-muconic acid, and animal feed (Lynd, L. R., Wyman, C. E., and Gerngross, T. U., Biocommodity Engineering, Biotechnol. Prog., 15: 777-793, 1999; and Philippidis, G. P., Cellulose bioconversion technology, in Handbook on Bioethanol: Production and Utilization, Wyman, C. E., ed., Taylor & Francis, Washington, D.C., 179-212, 1996; and Ryu, D. D. Y., and Mandels, M., Cellulases: biosynthesis and applications, Enz. Microb. Technol., 2: 91-102, 1980).

Potential coproducts may also be produced, such as multiple organic products from fermentable carbohydrate. Lignin-rich residues remaining after pretreatment and fermentation can be converted to lignin-derived chemicals, chemical building blocks or used for power production.

Conventional methods of fermentation and/or saccharification are known in the art including, but not limited to, saccharification, fermentation, separate hydrolysis and fermentation (SHF), simultaneous saccharification and fermentation (SSF), simultaneous saccharification and cofermentation (SSCF), hybrid hydrolysis and fermentation (HHF), and direct microbial conversion (DMC).

SHF uses separate process steps to first enzymatically hydrolyze cellulose to sugars such as glucose and xylose and then ferment the sugars to ethanol. In SSF, the enzymatic hydrolysis of cellulose and the fermentation of glucose to ethanol is combined in one step (Philippidis, G. P., in *Handbook on Bioethanol: Production and Utilization*, Wyman, C. E., ed., Taylor & Francis, Washington, D.C., 179-212, 1996). SSCF includes the cofermentation of multiple sugars (Sheehan, J., and Himmel, M., Bioethanol, Biotechnol. Prog. 15: 817-827, 1999). HHF includes two separate steps carried out in the same reactor but at different temperatures, i.e., high temperature enzymatic saccharification followed by SSF at a lower temperature that the fermentation strain can tolerate. DMC combines all three processes (cellulase production, cellulose hydrolysis, and fermentation) in one step (Lynd, L. R., Weimer, P. J., van Zyl, W. H., and Pretorius, I. S., Microbiol. Mol. Biol. Reviews, 66: 506-577, 2002).

These processes may be used to produce target products from the readily saccharifiable biomass produced by the pretreatment methods described herein.

EXAMPLES

The methods described herein are illustrated in the following examples. From the above discussion and these examples, one skilled in the art can ascertain the essential characteristics of this invention, and without departing from the spirit and scope thereof, can make various changes and modifications of the invention to adapt it to various uses and conditions.

The following materials were used in the examples. All commercial reagents were used as received. Sulfuric acid, ammonium hydroxide, acetic acid, acetamide, yeast extract, glucose, xylose, sorbitol, MgSO4.7H2O, phosphoric acid and citric acid were obtained from Sigma-Aldrich (St. Louis, Mo.). The additives listed in Table 9 were obtained from Stepan Company (Northfield, Ill.).

Corn cob was purchased from Independence Corn By Products (ICBP Cob), Independence, Iowa. The seller stored the cob at 60° C. and milled and sieved the cob to ⅛". The dry mass content of the cob was about 92.5%. Another variety of cob referred to as MDO7 cob was obtained from University of Wisconsin Farm, in Madison, Wis. and was milled to assorted sizes. [0062]The following abbreviations are used: "HPLC" is High Performance Liquid Chromatography, "C" is Centigrade, "kPa" is kiloPascal, "m" is meter, "mm" is millimeter, "kW" is kilowatt, "μm" is micrometer, "μL" is microliter, "mL" is milliliter, "L" is liter, "min" is minute, "mM" is millimolar, "cm" is centimeter, "g" is gram(s), "mg" is milligrams, "kg" is kilogram, "wt" is weight, "wt %" means weight percent "h" is hour(s), "temp" or "T" is temperature, "theoret" is theoretical, "pretreat" is pretreatment, "DWB" is dry weight of biomass, "ASME" is the American Society of Mechanical Engineers, "s.s." is stainless steel, "PEG" is polyethylene glycol.

Carbohydrate Analysis of Biomass

A modified version of the National Renewable Energy Laboratory, Laboratory Analytical Procedures (NREL LAP) for standard biomass analysis, "Determination of Structural Carbohydrates and Lignin in Biomass" was used to determine the weight percent glucan and xylan in the biomass. Sample preparation was simplified by drying at 80 ° C. under vacuum or at 105 ° C. under ambient pressure overnight. The samples were knife milled to pass through a 20 mesh screen but were not sieved. The dry milled solids were than subjected to the acid hydrolysis procedure at a 50 mg solids scale. The solids were not first extracted with water or ethanol. HPLC analysis of sugars was done on an Aminex HPX-87H column and no analysis of lignin was attempted.

The soluble sugars glucose, cellobiose, and xylose in saccharification liquor were measured by HPLC (Waters Alliance Model, Milford, Mass.) using Bio-Rad HPX-87H column (Bio-Rad Laboratories, Hercules, Calif.) with appropriate guard columns, using 0.01 N aqueous sulfuric acid as the eluant. The sample pH was measured and adjusted to 5-6 with sulfuric acid if necessary. The sample was then passed through a 0.2 μm syringe filter directly into an HPLC vial. The HPLC run conditions were as follows:

Biorad Aminex HPX-87H (for carbohydrates):
  Injection volume: 10-50 μL, dependent on concentration and detector limits Mobile phase: 0.01 N aqueous sulfuric acid, 0.2 micron filtered and degassed
Flow rate: 0.6 mL/minute
Column temperature: 50° C., guard column temperature <60° C.
Detector temperature: as close to main column temperature as possible
Detector: refractive index
Run time: 15 minute data collection After the run, concentrations in the sample were determined from standard curves for each of the compounds.

General Procedure for Delignification of Corn Cob

Corn cob was suspended in a specified volume of deionized water containing a specified weight of nucleophilic base and then mixed with a mechanical stirrer. The slurry was heated to the desired temperature for a specified time. Following this the reaction mixture was cooled to 50° C., vacuum filtered, and the solid residue was washed with deionized water. The solid residue was dried at room temperature either under ambient condition or laboratory vacuum (20 mm Hg). The dry mass content of the solid residue was determined by weighing a known weight of sample and heating to 99° C. under nitrogen atmosphere until constant weight was achieved.

Example 1

Production of Concentrated Sugar Solution from Corn Cob

Delignification of the corn cob: Corn cob (MDO7, 2.5 kg, moisture content 10%) was slowly added to a stirred solution of 2% sodium hydroxide solution (10 L). The amount of sodium hydroxide (NaOH) was 8.0 weight percent relative to the weight of corn cob. The initial pH of the solution was 12.3. The mixture was heated to reflux and maintained under reflux for 20 h. The reaction mixture was allowed to cool to 60° C. The reaction pH at this point was 9.80. A portion of the mixture (200 g) was set aside. The remainder of the mixture was transferred to a filter funnel with the aid of additional 1.9 kg water and filtered under laboratory vacuum. The filtrate was kept separately for analysis. The solid residue from the filtration was washed with water (4×5 L) and re-suspended in deionized water (10 L). The pH of the suspension was maintained at 5.0 for 2 hours by one addition of 37% HCl (2.5 mL). The suspension was then filtered. After draining off most of the liquid, the solid was collected and stored at room temperature.

The weight of the solid recovered was 5.31 kg. A portion of the solid was dried at 99° C. under nitrogen atmosphere for 4 h to determine the dry matter content of the cake, which was determined to be 25.9%. Further drying of the cake prior to saccharification was done under atmospheric pressure and at ambient temperature for 4 days.

The glucan and xylan content of the cob before and after delignification was determined by the NREL methods, well established in the art, and were found to be as follows:
Raw cob=39.2 wt % glucan; 28 wt % xylan
Delignified cob=51 wt % glucan, 38 wt % xylan
The weight ratio of glucan to xylan in the raw cob was 1.40. The weight ratio of glucan to xylan in the delignified cob was 1.34.

Saccharification of the delignified cob under high solid loading (22.6 wt %): The dried, delignified cob from the procedure above (208.9 g total, moisture content 16.2 wt %) was used for saccharification. A portion of the solid (155.4 g) was added to a solution of aqueous polyethylene glycol (1.25 g PEG, molecular weight 2000), and the suspension was heated to 50° C. with good mixing. The pH of the slurry was adjusted to 5.0 by the addition of 2% aqueous sulfuric acid (10.6 g of solution) followed by the addition of Accellerase™ 1000 cellulase (14.86 ml, protein concentration 97 mg/mL) and Multifect® CX 12L enzyme (11.6 mL, protein concentration 56 mg/mL). The reaction was continued at this temperature and pH (1.28 g of 2% aqueous sulfuric acid was added to maintain this pH). After 3 h, the remainder of the delignified cob (53.5 g, moisture content 16.2 wt %) and additional Accellerase™ 1000 cellulase (5.14 mL) and Multifect® CX 12L enzyme (3.9 mL) were added, followed by addition of a 0.512% aqueous solution of Penicillin G (0.5 mL, 2.5 ppm) and 2.1% aqueous solution of Virginiamycin (0.1 mL, 2 ppm). The reaction was continued with good mixing at 50° C. and at pH 5.0 (6.42 g of 2% aqueous sulfuric acid was added to maintain the pH at 5.0). Samples were withdrawn at intervals of 24, 48, 72, 96, and 117 h from the time of the last addition of solid. The sample was diluted 10 times (on a weight basis), filtered through 0.2 micron filter, and the filtrate was analyzed by HPLC as described in the General Methods for glucose, xylose, and cellobiose and compared to a standard aqueous solution glucose (8.8 mg/g), xylose (8.9 mg/g), and cellobiose (8.8 mg/g). From this, the saccharification yield and sugar titer was calculated. The results are shown in the following Tables.

TABLE 1

Cellobiose, glucose, and xylose concentrations at various saccharification reaction times as determined by HPLC analysis.
CONCENTRATIONS (mg/g of reaction mixture)

| | Time (h) | | | |
|---|---|---|---|---|
| Component | 24 | 48 | 72 | 117 |
| Cellobiose | 0.0 | 0.0 | 0.0 | 0.0 |
| Glucose | 54.0 | 72.0 | 82.3 | 106.0 |
| Xylose | 56.3 | 62.5 | 63.1 | 71.8 |
| Lactic Acid | 0.0 | 0.0 | 0.0 | 0.2 |

TABLE 2

Total mass of sugar monomers produced in the saccharification reaction with time.
TOTAL MASS (g)

| | Time (h) | | | |
|---|---|---|---|---|
| | 24 | 48 | 72 | 117 |
| Glucose | 41.7 | 55.7 | 63.6 | 82.0 |
| Xylose | 43.5 | 48.3 | 48.8 | 55.5 |
| Total Sugar | 85.3 | 104.0 | 112.4 | 137.5 |

TABLE 3

Glucose, xylose, combined saccharification (total sugar) percent yields, and percent sugar titer with time.

SACCHARIFICATION PERCENT YIELD

| | 24 h | 48 h | 72 h | 117 h |
|---|---|---|---|---|
| Glucose | 42.1 | 56.2 | 64.2 | 82.7 |
| Xylose | 57.4 | 63.7 | 64.3 | 73.2 |
| Total Sugar | 48.8 | 59.5 | 64.3 | 78.6 |

TABLE 3-continued

Glucose, xylose, combined saccharification (total sugar) percent yields, and percent sugar titer with time.

| Sugar Titer (%) | | | |
|---|---|---|---|
| 24 h | 48 h | 72 h | 117 h |
| 11.0 | 13.5 | 14.5 | 17.8 |

Example 2

Polysaccharide Enrichment and Delignification Of Corn Cob by Treatment with Sodium Hydroxide at 5.1, 8.0 and 20.0% Wt. % (Relative to Weight of Cob) and Comparison of Saccharification Performance 5.1% Sodium hydroxide treatment (5.1 wt % NaOH relative to weight of cob): Corn cob (ICBP, 100 g, milled to 2 mm) was suspended in 0.85% aqueous sodium hydroxide (200 mL, pH 13.0) and heated to 110° C. for 18 h. When the pH was checked at this time, it was nearly neutral. Another 200 mL of 0.85% aqueous sodium hydroxide and solid sodium hydroxide (1.7 g) were added and the heating was continued with occasional shaking of the flask. After 24 h, the hot solution was filtered and extensively washed with water. Though brown color eluted out with the filtrate, the solid material was brown colored indicating the presence of lignin adsorbed to the material. Also, the corn cob pellets retained their shape without as much chemical milling occurring as seen in pretreatment with higher concentrations of NaOH solution. The residue was suspended in water and the pH of the solution was adjusted to pH 5.0 with 20% aqueous citric acid. The residue was filtered and dried at room temperature under laboratory vacuum for 24 h. Yield of solid was 70.3 g. The sample was determined to have 6% moisture content.

8.0% Sodium hydroxide treatment (8.0 wt % NaOH relative to weight of cob): Corn cob (ICBP, 100 g, milled to 2 mm) was suspended in 2% aqueous sodium hydroxide and heated to 110° C. for 24 h. The solution was filtered hot and the residue washed with water to neutral pH and dried under laboratory vacuum for 48 h. The weight of pale yellow powder was 79.3 g. The moisture content of the solid was 20%.

A portion of the dried solid (42.0 g) was suspended in water (500 ml) and the pH (9.5) was lowered to 5.0 by the addition of 10% aqueous citric acid solution. After 45 min at this pH the suspension was filtered, washed with water and dried under laboratory vacuum. The moisture content of this material was 7%.

20.0% Sodium hydroxide treatment (20.0 wt % NaOH relative to weight of Cob): Corn cob (ICBP, 1000 g, milled to 2 mm size) was suspended in 5% aqueous sodium hydroxide (4000 mL) and heated to 110° C. for 16 h. The dark brown liquid was filtered hot and much of the liquid on the solid was drained under laboratory vacuum. The solid residue on the filter was washed with water until no more color eluted out. The solid was dried under laboratory vacuum for 24 hours.

100 gram of the above sample was suspended in water (700 mL) and stirred. The pH of the solution was 11.2. Aqueous citric acid solution (10%) was added to lower the pH to 5.0 and the suspension was stirred for 30 min. The solid was then filtered, washed with water and dried under vacuum at room temperature for 24 hours. After drying, 86.2 g of polysaccharide enriched biomass was obtained. The moisture content of this material was 7.3 wt %.

Glucan/xylan ratios, glucan wt %, xylan wt %, lignin wt %, and the percentage total carbohydrate content before and after sodium hydroxide treatment, as determined by the NREL methods for carbohydrate analysis, are presented in Table 4. The pretreatments with 5.1 and 8.0 weight percent NaOH relative to the weight of the biomass used show delignification of the biomass while maintaining a glucan/xylan weight ratio within 15% of that for the untreated biomass.

TABLE 4

Results for Polysaccharide Enriched Biomass Obtained by NaOH Pretreatments (Example 2).

| Sample | Glucan/Xylan weight Ratio | Glucan (wt %) | Xylan (wt %) | Lignin (wt %) | % Total Carbohydrate in the Biomass |
|---|---|---|---|---|---|
| Untreated corn cob | 1.33 | 37.5 | 28.74 | 13.88 | 66 |
| 5.1% NaOH | 1.33 | 47.8 | 35.8 | ND [1] | 84 |
| 8.0% NaOH | 1.35 | 52.96 | 39.11 | 3.33 | 92 |
| 20% NaOH | 1.84 | 58.55 | 31.86 | 5.43 | 90 |

Note:
[1] ND means "not determined"

Comparative saccharification of solid fractions of polysaccharide enriched biomass samples obtained by treatment with 5.1, 8.0, and 20% NaOH relative to the weight of the cob: Polysaccharide enriched biomass samples (1.0 g, moisture content 7-8%) obtained as solids from each of the 5.1 wt %, 8.0 wt %, and 20.0 wt % sodium hydroxide treatment cases were separately suspended in 50 mM citrate buffers (pH 5.0, 6.4 ml). Spezyme® (Genencor) cellulase solutions (100 µL, protein concentration 150 mg/mL) and Multifect® CX 12L enzyme (100 µL, protein concentration 45 mg/mL) were added to each buffer and the suspensions kept at 55° C. in a rotating oven. Samples (100 µL) were withdrawn at intervals of 24 h, 72 h, and 144 hours (6 days) and diluted to 1 ml with de-ionized water, filtered through 0.2 micron filter and subjected to HPLC analysis. At the end of the sixth day, each reaction mixture was filtered. The insoluble residue was dried in an oven at 99° C. for 24 h, where as the filtrate was lyophilized to determine the solid content.

Figure 1:
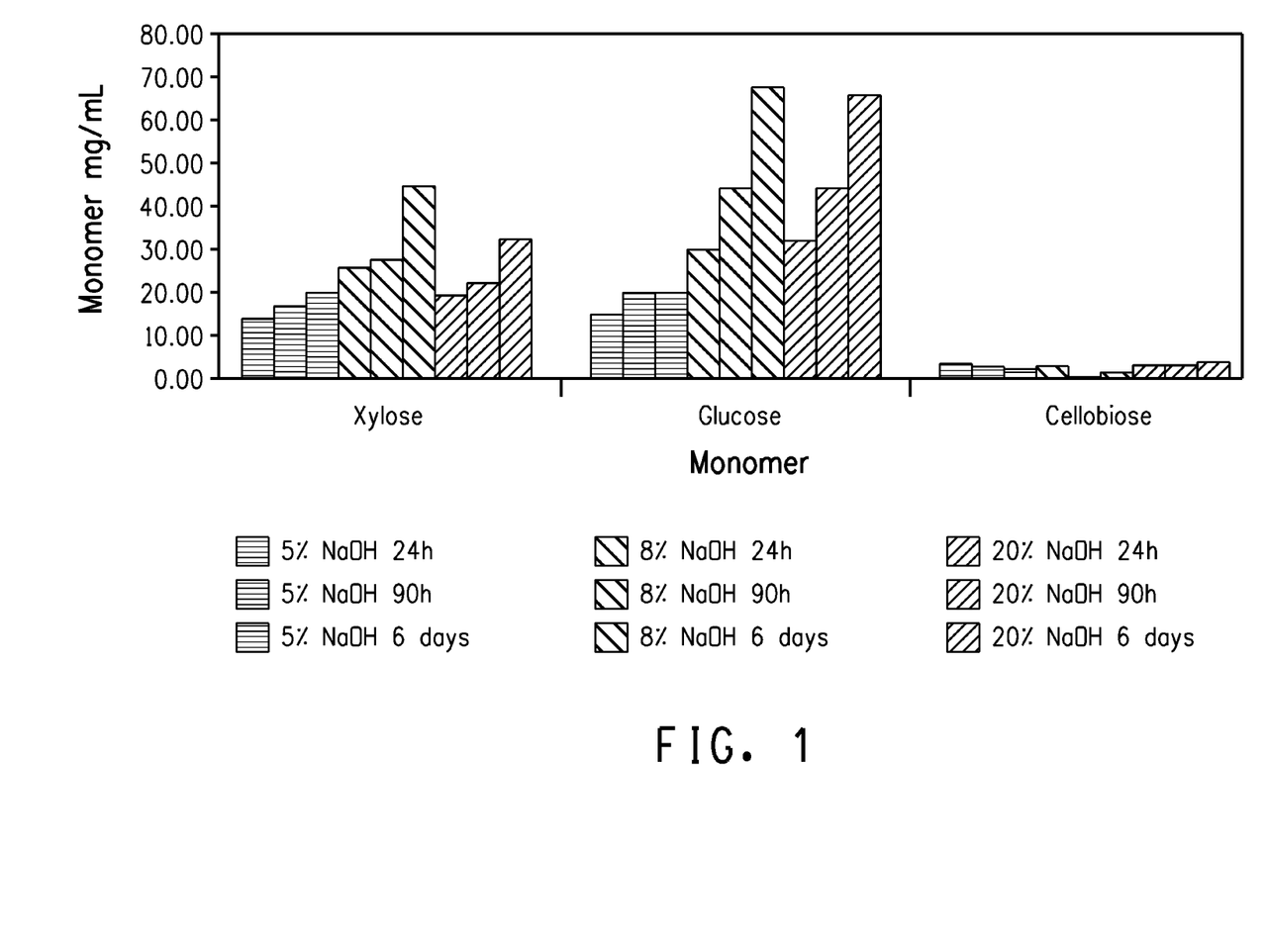
FIG. 1 is a graphical representation of the results for Example 2 showing the amount of xylose and glucose produced upon saccharification of corn cob delignified with 5.1 weight percent, 8.0 weight percent, and 20.0 weight percent sodium hydroxide (relative to the weight of the cob).

Results are presented in Table 5, Table 6, and FIG. 1, which is a graphical representation of the data in Table 5. As evident from the Tables and FIG. 1, biomass delignified with 8.0 weight percent and 20.0 weight percent NaOH, relative to the weight of the corn cob, produced the maximum amount of soluble sugars xylose and glucose, whereas the 5.1% NaOH treated material was more resistant to hydrolysis.

TABLE 5

Xylose, glucose, and cellobiose in mg/mL of the saccharification mixture analyzed at 24, 90, and 144 hours of reaction time from the polysaccharide enriched biomass samples obtained by treatment with 5.1 wt %, 8.0 wt %, and 20 wt % NaOH relative to the weight of the cob.

| Sample | Time (h) | Xylose (mg/mL) | Glucose (mg/mL) | Cellobiose (mg/mL) |
|---|---|---|---|---|
| 5.1 wt % NaOH | 24 | 13.23 | 15.04 | 3.61 |
| | 90 | 16.30 | 20.26 | 2.62 |
| | 144 | 19.63 | 20.37 | 2.24 |
| 8.0 wt % NaOH | 24 | 25.88 | 29.63 | 2.61 |
| | 90 | 27.85 | 43.99 | 0.20 |
| | 144 | 44.80 | 67.54 | 1.03 |
| 20.0 wt % | 24 | 19.00 | 32.20 | 3.02 |

TABLE 5-continued

Xylose, glucose, and cellobiose in mg/mL of the saccharification mixture analyzed at 24, 90, and 144 hours of reaction time from the polysaccharide enriched biomass samples obtained by treatment with 5.1 wt %, 8.0 wt %, and 20 wt % NaOH relative to the weight of the cob.

| Sample | Time (h) | Xylose (mg/mL) | Glucose (mg/mL) | Cellobiose (mg/mL) |
|---|---|---|---|---|
| NaOH | 90 | 21.19 | 44.16 | 2.90 |
| | 144 | 32.18 | 65.96 | 3.77 |

TABLE 6

Weight in grams of insoluble residue left behind after 144 hours of saccharification of polysaccharide enriched biomass obtained by treatment with 5.1 wt %, 8.0 wt %, and 20.0 wt % NaOH.

| Sample from Pretreatment with | Insoluble Residue Remaining (g) |
|---|---|
| 5.1 wt % NaOH | 0.61 |
| 8.0 wt % NaOH | 0.07 |
| 20.0 wt % NaOH | 0.14 |

| Sample from Pretreatment with | Soluble Content in the Filtrate (g) |
|---|---|
| 5.1 wt % NaOH | 0.53 |
| 8.0 wt % NaOH | 1.07 |
| 20.0 wt % NaOH | 0.92 |

Also, weight in grams of solid content of the filtrate for each case.

Example 3

Comparison of Saccharification Efficiency Of 8% NaOH Delignified Corn Cob with/and Without Removal Of Soluble Lignin, to Show Detrimental Effect of Lignin on Saccharification Efficiency Two vials, each containing 1 gram of raw cob (ICBP) in 4 mL of 2% aqueous NaOH solution were refluxed at 110° C. for 24 h. The amount of NaOH used was 8 weight percent relative to the weight of the corn cob. The liquid from vial 1 was pipetted out and washed with deionized water (4×2 mL) and filtered (total volume of the filtrate was 10.5 mL, against expected 12 mL, indicating the retention of 1.5 mL in the solid). It was then suspended in citrate buffer (4.9 mL) and 20% citric acid solution (0.040 mL) was added to get a pH of 5.0. To vial 2, 20% citric acid solution (0.4 mL) was added followed by the addition of citrate buffer (2 mL) to get a pH of 5.0. Both solid residues were then saccharified with an enzyme cocktail (180 µL) containing Spezyme® (9 mg), Multifect®CX 12L (2.7 mg) and Novozyme 188 (3 mg) at 50° C. Samples were withdrawn at the end 1, 2, and 5 days and the sugar monomer content was determined by HPLC as described above. As can be seen from Table 7, the removal of lignin facilitated higher production of sugars.

TABLE 7

Total fermentable sugars (glucose and xylose, mg) produced in delignified cob sample containing no lignin (Sample 1 and 1-Duplicate) and lignin (Sample 2 and 2-Duplicate.

| Sample | 1 day (mg) | 2 days (mg) | 5 days (mg) |
|---|---|---|---|
| 1 | 342 | 411 | 446 |
| 1-Duplicate | 337 | 407 | 436 |
| 2 | 250 | 307 | 402 |
| 2-Duplicate | 245 | 295 | 398 |

Example 4

Enhancement of Yield by Commercial Additives in Saccharification of Delignified Corn Cob with Enzyme Cocktail at High (25 Mg/G Dry Biomass [DB]) & Low Enzyme (8.4 Mg/G DB) Loading Delignification of corn cob with 8 percent by weight NaOH relative to cob followed by pressure filtration: Corn cob (ICBP, 400 g, moisture content 5%) was suspended in 3.2% sodium hydroxide solution (1000 mL) and refluxed for 24 hrs at 110° C. The reaction mixture was cooled and the contents transferred in three portions to a pressure filtration system. The slurry was initially pressure filtered under air at 10 psi followed by final dewatering at 220 psi. This afforded three cakes with the indicated wet mass, dry mass, and percent solid in the wet cake (on a dry basis). No attempt was made to further wash the cakes.

TABLE 8

Weight of the wet cake and the solid content of the delignified corn cob obtained after pressure filtration of the reaction slurry with no further water washing of the cakes

| Run | Cake Mass (g) Wet | Cake Mass (g) Dry | % Solids |
|---|---|---|---|
| 1 | 175 | 73 | 41.5% |
| 2 | 202 | 84 | 41.6% |
| 3 | 212 | 81 | 38.3% |
| Total | 589 | 238 | |

Evaluation of additive effect on the saccharification efficiency of delignified corn cob: The following procedure was used to evaluate the effect of each of the additives listed in Table 9 on the saccharification of the delignified biomass. Delignified corn cob (2.40 g, moisture content 58.4%, dry mass equivalent 1 gram) was suspended in 50 mM sodium citrate buffer (4.35 mL, pH 5.0). The sample pH was adjusted to pH 5.0 with 20% aqueous citric acid (0.1 mL). An aqueous solution of the additive (5%, 0.1 mL) and the enzyme solution (0.295 mL) containing the desired amount protein (see Table 10) was added and the solution was incubated at 50° C. Samples were analyzed at the end 1, 2, and 4 days by HPLC using an Aminex HPX-87H column and 0.01 N $H_2SO_4$ as the mobile phase. Results are reported in Tables 11 and 12.

TABLE 9

List of additives used in saccharification of delignified biomass

| Sample | Additive | Description | % Actives |
|---|---|---|---|
| 1 | Control [no additive] | | |
| 2 | Agent X-2776-45-1 | Fatty acid methyl ester | |
| 3 | AMPHOSOL ® 160C-30 | Sodium lauriminodipropionate | 37.5 |
| 4 | AMPHOSOL ® 1C | Sodium Cocoamphoacetate | 30 |
| 5 | CEDEPAL ® TD-403MFLD | Sodium tridecyl ether sulfate | 50 |
| 6 | NINEX ® MT-603 | Fatty acid ethoxylate, POE-3 | 100 |
| 7 | NINEX ® MT-615 | Fatty acid ethoxylate, POE-15 | 70 |
| 8 | STEOL ® CS-270 | Sodium laureth sulfate (2 EO) | 28 |
| 9 | STEOL ® CS-330 | Sodium laureth sulfate | 100 |
| 10 | STEPAN ® 108 | Caprylic/capric triglyceride | 100 |
| 11 | STEPAN ® C-25 | Methyl caprylate/caprate | 100 |
| 12 | STEPAN ® C-40 | Methyl laurate | 100 |
| 13 | STEPAN ® C-65 | Methyl palmitate/oleate | 100 |
| 14 | Stepanate AXS | Ammonium xylene sulfonate | 42 |
| 15 | STEPSPERSE ® DF-100 | Nonionic/lignosulfonate blend | 100 |
| 16 | STEPSPERSE ® DF-200 | Anionic/lignosulfonate blend | 100 |
| 17 | STEPSPERSE ® DF-400 | Nonionic/lignosulfonate blend | 100 |
| 18 | STEPSPERSE ® DF-500 | Anionic/lignosulfonate blend | 100 |
| 19 | STEPSPERSE ® DF-600 | Nonionic/lignosulfonate blend | 100 |
| 20 | Stepanate SXS | Sodium xylene sulfonate | 41 |
| 21 | STEPOSOL ® ROE-W | Canola oil, methyl ester | 100 |
| 22 | STEPOSOL ® SB-W | Soybean oil, methyl ester | >99 |
| 23 | PEG 2000 | Polyethylene glycol | |
| 24 | PEG 6000 | Polyethylene glycol | |
| 25 | PEG 8000 | Polyethylene glycol | |
| 26 | NINEX ® MT-610 | Fatty Acid Ethoxylate, POE-10 | 100 |
| 27 | NINEX ® MT-630F | Fatty Acid Ethoxylate, POE-30 | 100 |

TABLE 10

Enzymes used for each enzyme loading (high and low)

| | Enzyme Used (mg/g delignified cob) | | |
|---|---|---|---|
| Enzyme Loading | Accellerase ™1000 | Multifect ® CX 12L | Total |
| High | 20.0 | 5.0 | 25.0 |
| Low | 6.7 | 1.7 | 8.4 |

TABLE 11

Observed Percentage increase in total sugar monomers relative to control upon including additive (0.5% relative to weight of corn cob) in enzymatic saccharification of delignified biomass at high enzyme loading.

| | | Time (d) | | | |
|---|---|---|---|---|---|
| Sample | Surfactant | 1 | 2 | 3 | 4 |
| TOTAL SUGAR MONOMER MASS (mg) - HIGH LOADING | | | | | |
| Average | Control | 440.1 | 557.6 | 591.3 | 625.0 |
| % INCREASE IN TOTAL SUGAR MONOMER MASS - HIGH LOADING | | | | | |
| 2 | Agent X-2776-45-1 | 4.6 | 3.3 | 3.4 | 2.6 |
| 3 | AMPHOSOL ® 160C-30 | 5.7 | 5.0 | 3.3 | 4.0 |
| 4 | AMPHOSOL ® 1C | 6.4 | 4.4 | 4.0 | 3.1 |
| 5 | CEDEPAL ® TD-403MFLD | 1.8 | 4.8 | 1.5 | 1.4 |
| 6 | NINEX ® MT-603 | 2.3 | 4.4 | 3.9 | 3.1 |
| 7 | NINEX ® MT-615 | 22.2 | 8.7 | 6.2 | 6.2 |
| 8 | STEOL ® CS-270 | 5.8 | 2.8 | 3.5 | 2.0 |
| 9 | STEOL ® CS-330 | 7.1 | 3.1 | 3.0 | 1.9 |
| 10 | STEPAN ® 108 | 6.1 | 3.6 | 6.3 | 2.3 |
| 11 | STEPAN ® C-25 | 5.7 | 3.7 | 4.0 | 4.1 |
| 12 | STEPAN ® C-40 | 7.3 | 3.0 | 3.8 | 1.0 |
| 13 | STEPAN ® C-65 | 5.6 | 3.7 | 2.5 | 3.1 |
| 14 | Stepanate AXS | 7.4 | 2.1 | 1.8 | 1.6 |
| 15 | STEPSPERSE ® DF-100 | 10.0 | 6.5 | 6.1 | 2.6 |
| 16 | STEPSPERSE ® DF-200 | 8.4 | 6.3 | 2.7 | 2.2 |
| 17 | STEPSPERSE ® DF-400 | 4.1 | 2.8 | 2.6 | 2.2 |
| 18 | STEPSPERSE ® DF-500 | 3.1 | 2.5 | 1.6 | 1.0 |
| 19 | STEPSPERSE ® DF-600 | 5.6 | 5.5 | 3.4 | 2.3 |
| 20 | Stepanate SXS | 7.3 | 4.8 | 2.9 | 1.2 |
| 21 | STEPOSOL ® ROE-W | 7.9 | 1.3 | 1.2 | -1.2 |
| 22 | STEPOSOL ® SB-W | 6.4 | 1.9 | 1.0 | -2.0 |
| 23 | PEG 2000 | 20.7 | 9.4 | 8.0 | 5.5 |
| 24 | PEG 6000 | 17.5 | 7.5 | 6.4 | 4.0 |
| 25 | PEG 8000 | 19.5 | 7.6 | 6.9 | 4.7 |
| 26 | NINEX ® MT-610 | 8.6 | 10.1 | 9.5 | 9.8 |
| 27 | NINEX ® MT-630F | 20.4 | 17.2 | 12.1 | 8.5 |

Reaction mixture analyzed by HPLC: end of days 1-4

TABLE 12

Observed percentage increase in total sugar monomers relative to control upon the inclusion of additives (0.5% relative to weight of corn cob) in the enzymatic saccharification of delignified biomass at low enzyme loading.

| | | Time (d) | | | |
|---|---|---|---|---|---|
| Sample | Surfactant | 1 | 2 | 3 | 4 |
| TOTAL SUGAR MONOMER MASS (mg) - LOW LOADING | | | | | |
| Average | Control | 232.2 | 314.0 | 367.3 | 411.8 |
| % INCREASE IN TOTAL SUGAR MONOMER MASS - LOW LOADING | | | | | |
| 2 | Agent X-2776-45-1 | 2.7 | 3.0 | 1.1 | -0.4 |
| 3 | AMPHOSOL ® 160C-30 | 8.7 | 12.2 | 9.1 | 9.5 |
| 4 | AMPHOSOL ® 1C | -1.6 | 2.1 | 5.4 | 5.5 |
| 5 | CEDEPAL ® TD-403MFLD | -3.7 | 3.7 | 2.2 | 3.1 |
| 6 | NINEX ® MT-603 | -1.7 | 4.4 | 5.7 | 4.5 |
| 7 | NINEX ® MT-615 | 9.8 | 16.2 | 15.5 | 9.2 |
| 8 | STEOL ® CS-270 | -5.5 | 0.7 | 0.1 | -1.2 |
| 9 | STEOL ® CS-330 | -1.7 | 9.7 | 2.9 | 3.7 |
| 10 | STEPAN ® 108 | -4.2 | 7.0 | 5.6 | 3.0 |
| 11 | STEPAN ® C-25 | -4.0 | 2.1 | 4.2 | 3.8 |
| 12 | STEPAN ® C-40 | -6.0 | 0.8 | 3.2 | 0.8 |
| 13 | STEPAN ® C-65 | 0.9 | 3.8 | 6.1 | 4.0 |
| 14 | STEPAN ® AXS | 1.6 | 3.8 | 4.7 | 2.7 |
| 15 | STEPSPERSE ® DF-100 | 15.2 | 9.6 | 10.5 | 7.0 |

TABLE 12-continued

Observed percentage increase in total sugar monomers relative to control upon the inclusion of additives (0.5% relative to weight of corn cob) in the enzymatic saccharification of delignified biomass at low enzyme loading.

| Sample | Surfactant | Time (d) | | | |
|---|---|---|---|---|---|
| | | 1 | 2 | 3 | 4 |
| 16 | STEPSPERSE ® DF-200 | 5.6 | 6.3 | 5.2 | 5.4 |
| 17 | STEPSPERSE ® DF-400 | 13.3 | 14.1 | 14.2 | 10.8 |
| 18 | STEPSPERSE ® DF-500 | 1.7 | −1.0 | 0.6 | 1.8 |
| 19 | STEPSPERSE ® DF-600 | 14.4 | 10.0 | 8.3 | 1.5 |
| 20 | STEPSPERSE ® SXS | 0.6 | 0.5 | 2.6 | 0.8 |
| 21 | STEPOSOL ® ROE-W | 1.0 | 0.5 | 3.0 | 1.0 |
| 22 | STEPOSOL ® SB-W | 7.3 | 2.5 | 4.8 | 6.9 |
| 23 | PEG 2000 | 36.1 | 25.8 | 27.3 | 21.6 |
| 24 | PEG 6000 | 31.2 | 23.6 | 21.8 | 18.7 |
| 25 | PEG 8000 | 30.4 | 21.6 | 19.3 | 15.8 |
| 26 | NINEX ® MT-610 | 16.8 | 13.5 | 10.0 | 7.3 |
| 27 | NINEX ® MT-630F | 22.4 | 15.1 | 14.2 | 10.7 |

Reaction mixture was analyzed at the end of days 1, 2, 3, and 4 by HPLC. Unexpectedly, the increment is much higher at low enzyme loading as compared to the high enzyme loading.

The list of best performing (over 10% increase in saccharification yield) additives under the conditions tested:
STEPSPERSE® DF-100
PEG 2000
PEG 6000
PEG 8000
NINEX® MT-610
NINEX® MT-630F Other additives which can also provide an increase in total sugar monomers relative to an additive-free control in the enzymatic saccharification of delignified biomass at low enzyme loadings include Tween 20 and Tween 80 (also known as polysorbate 20 and polysorbate 80, respectively). These additives are nonionic surfactants derived from polyethoxylated sorbitan and a fatty acid, for example lauric acid, oleic acid, or other $C_{12}$ to $C_{30}$ fatty acids. Additionally, additives such as secondary alcohol ethoxylates, fatty alcohol ethoxylates, nonylphenol ethoxylate, and tridecyl ethoxylates, as disclosed in U.S. Pat. No. 7,354,743 may be used.

Example 5

Enhancement of Enzymatic Saccharification of Delignified, Water Washed Corn Cob with Preferred Additives in Example 4 at Low Enzyme Loading (Less than 12 mg Protein/Gram Dry Delignified Corn Cob) and Absence of Additive Effect At High Enzyme Loading (Greater than About 25 mg Protein/Gram Dry Delignified Corn Cob)

Corn cob (ICBP, 100 g) was delignified with 2% aqueous sodium hydroxide solution as described in Example 1. Instead of isolating the polysaccharide enriched biomass by vacuum filtration, the reaction mixture was filtered under pressure (8 to 20 psi) to squeeze out the liquid, followed by washing with deionized water and finally compacting the residue at 220 psi air pressure in a filtration unit. This afforded 141.19 g of polysaccharide enriched, delignified biomass as a wet cake, which had 57.5% moisture content. The sugar analyses of the untreated cob and the solid fraction of the delignified polysaccharide enriched biomass obtained after sodium hydroxide pretreatment are shown in Table 13.

TABLE 13

Sugar Analyses (Example 5)

| Sample | % Glucan | % Xylan | % Total Sugars |
|---|---|---|---|
| Raw Cob | 37.5 | 28.7 | 66.2 |
| Delignified Cob | 52.3 | 39.8 | 92.1 |

A portion of the above cake (0.5 g) was suspended in 50 mM sodium citrate buffer (pH 5.0, 3.125 mL) containing a mixture of Accelerase™1000 cellulase and Multifect® CX 12L enzyme (protein ratio 3.94:1) mixture containing 4.20 mg, 5.85 mg or 12.50 mg of protein (corresponding respectively to 8.4 mg, 11.7 mg or 25 mg of protein per gram of dry delignified corn cob) in the presence or absence of additives PEG 2000 (Sigma-Aldrich, St. Louis, Mo.) or NINEX® MT-610 (fatty acid ethoxylate ester, Stepan Company, Northfield, Ill.). The additive concentration relative to the weight of dry biomass was 0.0%, 0.5% and 1.0% for each enzyme loading used. Table 14 summarizes the reaction conditions used for the saccharifications performed in Example 5.

Figure 2:
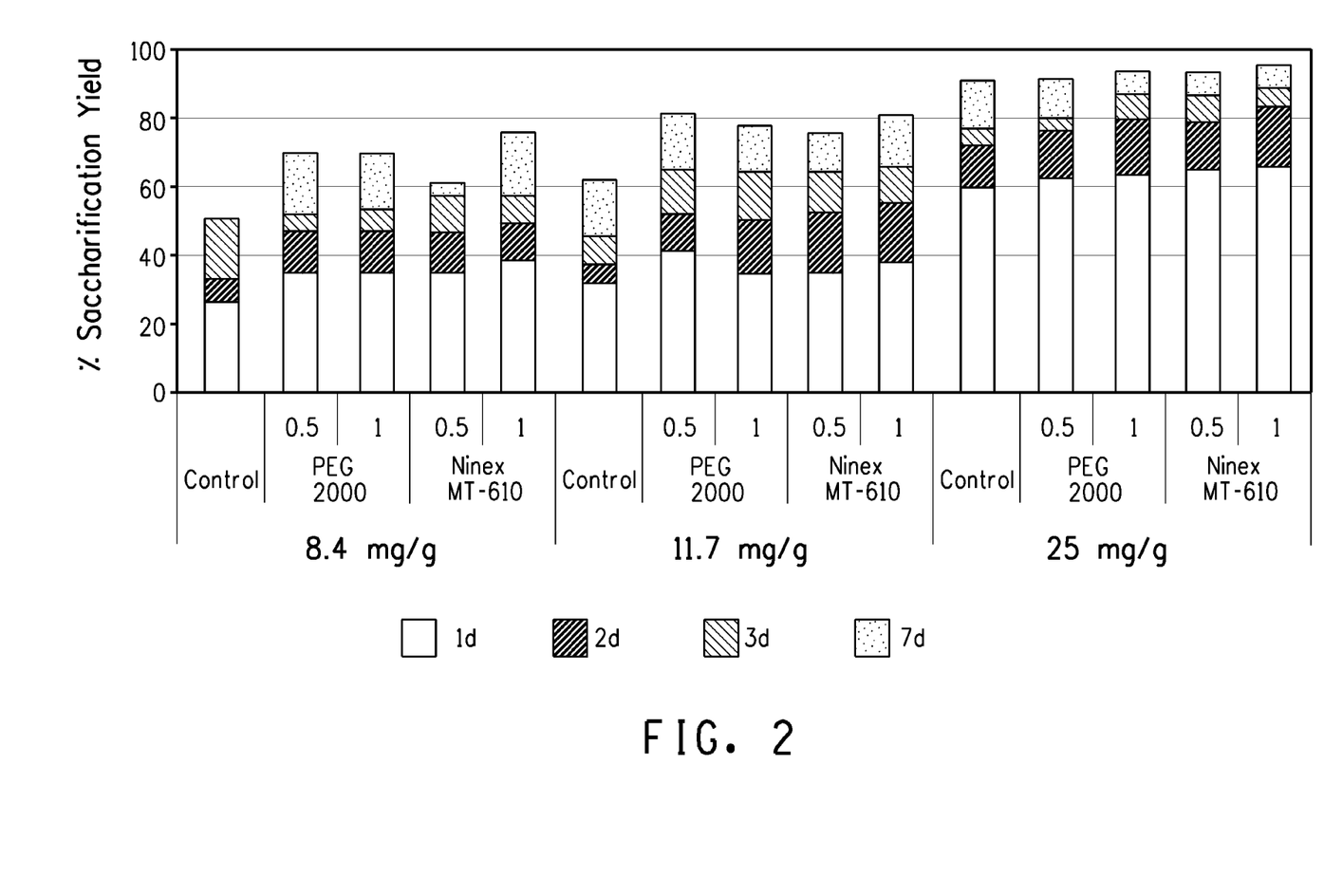
FIG. 2 is a graphical representation of the results for Example 5 showing the effect of additives PEG 2000 and NINEX® MT-610 with varying enzyme loading on the saccharification yield of delignified corn cob.

The reaction samples taken at intervals of 24 h, 48 h, 72 h, and 168 h (7 days) were analyzed by HPLC for glucose and xylose content. The results are reported as % yield in Table 15 and represented graphically in FIG. 2. The yields were calculated on the basis of expected total glucan and xylan present in the delignified corn cob. Table 16 shows the percentage increase in total sugar monomer mass produced with time for each sample.

These results show that the effect of the added additive to increase sugar yield is greatest with the lower enzyme loadings, for example at the loadings below about 25 mg/g.

TABLE 14

Reaction Conditions Used in Each Saccharification Performed for Example 5

| Example #[1] | Enzyme Loading[2] | Additive Used | Additive Loading[3] |
|---|---|---|---|
| 5A | 8.4 | None | 0 |
| 5B | 8.4 | PEG 2000 | 0.5 |
| 5C | 8.4 | PEG 2000 | 1.0 |
| 5D | 8.4 | NINEX ® MT-610 | 0.5 |
| 5E | 8.4 | NINEX ® MT-610 | 1.0 |
| 5F | 11.7 | None | 0 |
| 5G | 11.7 | PEG 2000 | 0.5 |
| 5H | 11.7 | PEG 2000 | 1.0 |
| 5J | 11.7 | NINEX ® MT-610 | 0.5 |
| 5K | 11.7 | NINEX ® MT-610 | 1.0 |
| 5L | 25 | None | 0 |
| 5M | 25 | PEG 2000 | 0.5 |
| 5N | 25 | PEG 2000 | 1.0 |
| 5P | 25 | NINEX ® MT-610 | 0.5 |
| 5Q | 25 | NINEX ® MT-610 | 1.0 |

Notes:
[1]Refers to saccharification runs of Example 5
[2]in mg of protein per gram of dry delignified corn cob
[3]additive concentration relative to the weight of dry delignified corn cob

TABLE 15

Yields of Total Sugars with Time for Saccharification of Polysaccharide Enriched, Delignified Biomass at Three Different Enzyme Loadings and with Two Different Surfactant Loadings.
SACCHARIFICATION % YIELD

| Enzyme Loading | Additive | Additive Loading (%) | Time (d) 1 | 2 | 3 | 7 |
|---|---|---|---|---|---|---|
| 8.4 mg/g | Control | | 24.0 | 30.0 | 45.9 | 44.3 |
| | PEG 2000 | 0.5 | 33.7 | 43.1 | 47.4 | 64.5 |
| | | 1.0 | 33.5 | 43.1 | 48.8 | 65.4 |
| | NINEX® | 0.5 | 32.8 | 44.0 | 54.3 | 57.7 |
| | MT-610 | 1.0 | 37.0 | 46.2 | 54.3 | 71.0 |
| 11.7 mg/g | Control | | 30.2 | 35.7 | 42.7 | 58.9 |
| | PEG 2000 | 0.5 | 38.4 | 50.4 | 61.3 | 76.3 |
| | | 1.0 | 33.8 | 48.2 | 59.7 | 73.4 |
| | NINEX® | 0.5 | 33.5 | 50.8 | 59.5 | 71.6 |
| | MT-610 | 1.0 | 36.2 | 53.6 | 62.3 | 76.2 |
| 25 mg/g | Control | | 56.3 | 71.0 | 74.2 | 83.1 |
| | PEG 2000 | 0.5 | 58.3 | 72.9 | 75.4 | 83.9 |
| | | 1.0 | 61.6 | 74.8 | 80.3 | 84.7 |
| | NINEX® | 0.5 | 62.3 | 74.6 | 80.3 | 84.8 |
| | MT-610 | 1.0 | 63.0 | 77.4 | 82.7 | 88.1 |

TABLE 16

Increase over control (absence of additives) in weight of total monomer sugars (glucose + xylose) on days 1, 2, 3, and 7, as result of additives PEG 2000 and NINEX® MT-610 on saccharification of delignified, polysaccharide enriched biomass with Accelerase™1000-Multifect® CX 12L at 3 different enzyme loadings and 2 additive concentrations
% INCREASE IN TOTAL SUGAR MONOMER MASS PRODUCED

| Enzyme Loading | Additive | Additive Loading (wt %) | Time (days) 1 | 2 | 3 | 7 |
|---|---|---|---|---|---|---|
| 8.4 mg/g | PEG 2000 | 0.5 | 40.6 | 43.9 | 3.4 | 45.6 |
| | | 1.0 | 39.9 | 43.7 | 6.3 | 47.5 |
| | NINEX® | 0.5 | 36.9 | 46.8 | 18.4 | 30.1 |
| | MT-610 | 1.0 | 54.1 | 54.3 | 18.4 | 60.2 |
| 11.7 mg/g | PEG 2000 | 0.5 | 27.0 | 41.3 | 43.5 | 29.5 |
| | | 1.0 | 12.0 | 35.2 | 39.6 | 24.6 |
| | NINEX® | 0.5 | 10.8 | 42.3 | 39.2 | 21.5 |
| | MT-610 | 1.0 | 19.8 | 50.1 | 45.8 | 29.3 |
| 25 mg/g | PEG 2000 | 0.5 | 3.6 | 2.6 | 1.7 | 1.0 |
| | | 1.0 | 9.4 | 5.3 | 8.2 | 2.0 |
| | NINEX® | 0.5 | 10.6 | 5.0 | 8.3 | 2.1 |
| | MT-610 | 1.0 | 11.9 | 9.0 | 11.5 | 6.1 |

What is claimed is:

1. A method of producing a concentrated sugar solution from biomass, the method comprising:
   a) delignifying biomass comprising the substeps of
      i) contacting with water and at least one nucleophilic base, a biomass comprising lignin and having a glucan/xylan weight ratio $G_1/X_1$ to form a biomass slurry having a pH of about 12.5 to about 13.0; and
      ii) maintaining the biomass slurry under reaction conditions such that the slurry attains a pH of about 9.5 to about 10.0 and has a glucan/xylan weight ratio $G_2/X_2$ within 10% of the value of $G_1/X_1$, and wherein the slurry comprises a lignin-containing liquid fraction and a solid fraction comprising a polysaccharide enriched biomass;

wherein $G_1$ and $G_2$ are grams of glucan per 100 grams of biomass and biomass slurry respectively, and $X_1$ and $X_2$ are grams of xylan per 100 grams of biomass and biomass slurry respectively; and
   wherein the water soluble metal hydroxide is selected from the group consisting of sodium hydroxide, and the metal carbonate or the organic hydroxide is selected from the group consisting of sodium carbonate, potassium carbonate, ammonium hydroxide; and
   wherein the reaction conditions include a temperature from about 20° C. to about 110° C. and a reaction time of about 4 hours to about 30 days; and
   b) adding an additive selected from the group consisting of polyethylene glycols, fatty acid esters, fatty acid ethoxylates, nonionic surfactants derived from polyethoxylated sorbitan and a fatty acid, sodium lauriminodipropionate, sodium cocoamphoacetate, sodium tridecyl ether sulfate, and a combination of these, such that the enzyme loading of the saccharification enzyme consortium is reduced relative to the loading of the saccharification enzyme consortium when none of the additives is added; and
   c) contacting with a saccharification enzyme consortium an aqueous suspension of at least a portion of the solid fraction of the polysaccharide enriched biomass,
      the solid fraction of the polysaccharide enriched biomass being 13 weight percent to about 30 weight percent of the aqueous suspension,
   at reaction conditions sufficient to produce a saccharification product comprising at least about 7 percent by weight sugars, based on the total weight of the saccharification product, in 24 hours of contact with the saccharification enzyme consortium.

2. The method of claim 1 wherein the saccharification product comprises at least about 18 percent by weight sugars in 168 hours.

3. The method of claim 1 wherein the additive is from about 0.1 weight percent to about 5 weight percent, based on the weight of the solid fraction of the polysaccharide enriched biomass solid fraction in the aqueous suspension.

4. The method of claim 3, wherein the additive is a polyethylene glycol of molecular weight 500 to 50,000 Daltons, a fatty acid ester selected from the group consisting of methyl esters of $C_{12}$ to $C_{30}$ fatty acid esters, fatty acid ethoxylates of $C_{12}$ to $C_{30}$ fatty acids, nonionic surfactants derived from polyethoxylated sorbitan and a $C_{12}$ to $C_{30}$ fatty acid, and a combination of these.

5. The method of claim 1 wherein at least about 70 percent of the lignin in the biomass is delignified in the solid fraction of the polysaccharide enriched biomass.

6. The method of claim 1 wherein the concentration of the solid fraction in the aqueous suspension is from about 21 weight percent to about 30 weight percent, and the saccharification product comprises sugars corresponding to at least a 65% saccharification yield based on the sum of glucan and xylan in the polysaccharide enriched biomass.

7. The method of claim 1 wherein the sugars comprise at least one sugar monomer selected from the group consisting of glucose, arabinose, xylose, mannose, and galactose, and a combination of these.

* * * * *